United States Patent
Won

Patent Number: 5,253,662
Date of Patent: Oct. 19, 1993

[54] DENTAL FLOSS HOLDER

[76] Inventor: Se K. Won, 6261 Glacier Dr., Westminster, Calif. 92683

[21] Appl. No.: 40,501

[22] Filed: Mar. 31, 1993

Related U.S. Application Data

[63] Continuation-in-part of Ser. No. 911,963, Jul. 10, 1992, Pat. No. 5,201,330.

[51] Int. Cl.$^5$ ............................................. A61C 15/00
[52] U.S. Cl. ................................... 132/325; 132/324
[58] Field of Search ............. 132/325, 323, 324, 327, 132/328

[56] References Cited

U.S. PATENT DOCUMENTS

| | | | |
|---|---|---|---|
| 1,454,429 | 5/1923 | Dresser | 132/325 X |
| 4,254,786 | 3/1981 | Won | 132/325 |
| 4,574,823 | 3/1986 | Uriss | 132/325 |
| 5,038,806 | 8/1991 | Ewald | 132/325 |
| 5,199,452 | 4/1993 | Cheng | 132/325 |
| 5,201,330 | 4/1993 | Won | 132/325 |

*Primary Examiner*—Gene Mancene
*Assistant Examiner*—Cindy A. Cherichetti
*Attorney, Agent, or Firm*—Robert R. Thornton

[57] ABSTRACT

A dental floss holder is provided with a slot-headed locking axle on which a spool of floss is mounted. A length of floss from the spool disposed within the holder passes through the axle slot and is spanned across two spaced prongs formed on the holder and locked to the axle by being wound on the axle beneath the slotted head after spanning. Tension is selectively manually applied to the spanned floss by the unidirectional rotation of locking cap which is held in position by the slotted head of the locking axle to provide a taut span of floss which can be manipulated between the user's teeth.

6 Claims, 3 Drawing Sheets

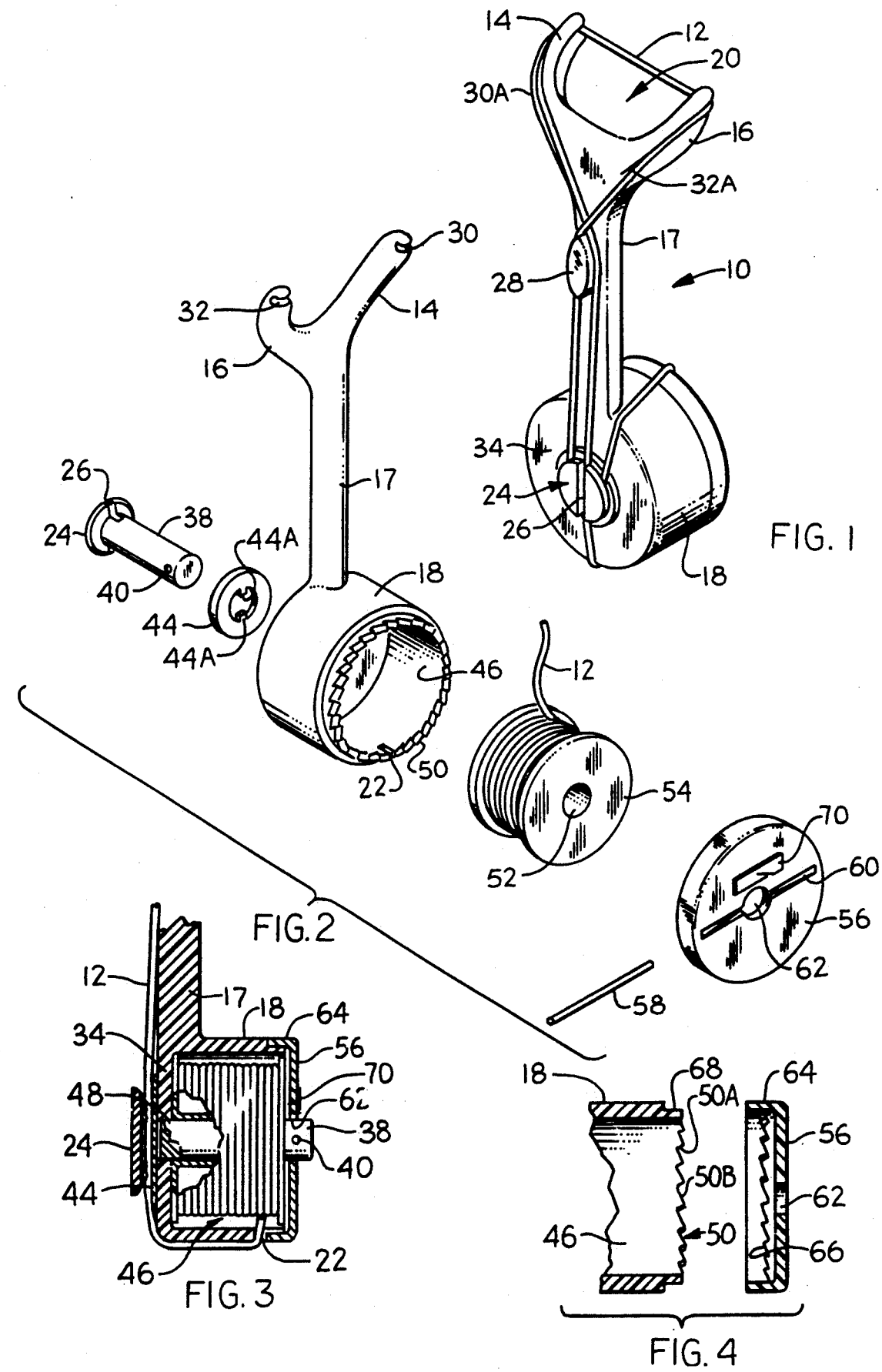

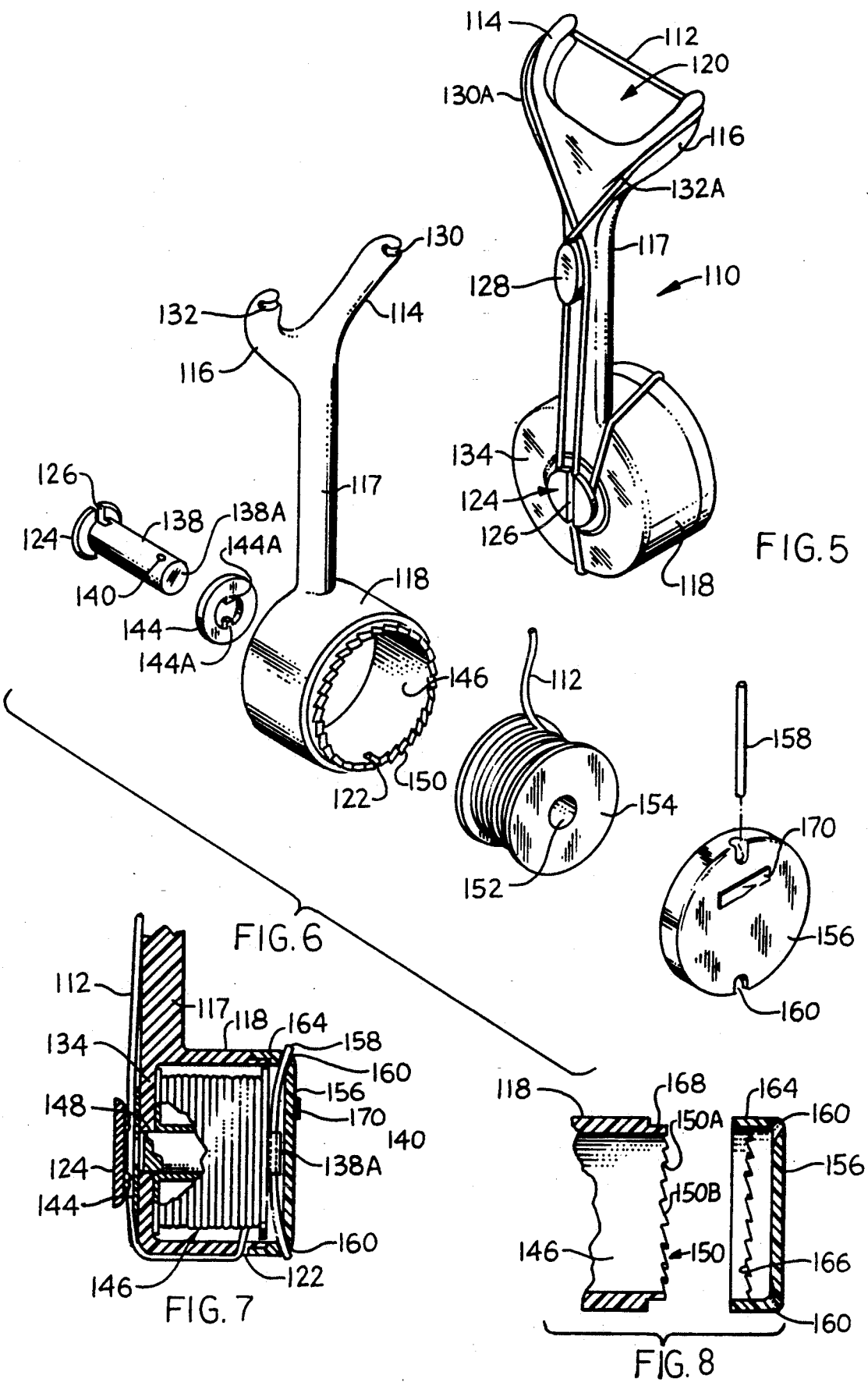

DENTAL FLOSS HOLDER

ROSS REFERENCE TO RELATED APPLICATION

This application is a continuation-in-part of my copending application Ser. No. 07/911,963, filed Jul. 10, 1992 now U.S. Pat. No. 5,201,330 for DENTAL FLOSS HOLDER.

BRIEF DESCRIPTION OF THE INVENTION

This invention relates to a dental floss holder containing a supply of floss and adapted to provide an exposed section of dental floss maintained under tension for cleaning between the user's teeth and constitute improvements of the Dental Floss Holder shown in my prior U.S. Pat. No. 4,254,786, issued Mar. 10, 1981.

In the holder described in U.S. Pat. No. 4,254,786, a length of floss wound on a spool is held within a body member is manually pulled from the spool. When a sufficient length has been unwound, the floss is wound about one side of a slotted head on a locking axle, threaded over two prongs on the holder, and wound about the other side of the slotted head. The locking axle is fixed in position by means of a racheting circular spring clip which engages ratcheting recesses formed in the bottom of the body member. Tension is applied to the floss when stretched between the two prongs by rotation of the locking axle. The taut floss can be manipulated between teeth when the holder is held by the user. However, in use, because of the strength of the spring, removal of the spring when it is necessary to replace the spool of floss has been extremely difficult, resulting in user dissatisfaction.

In the present invention, the ratcheting circular spring clip is replaced by a locking cap formed with a depending lip on the periphery of the cap so as to enclose the body member adjacent the ratcheting recesses. A transverse passageway in the axle contains a pin which extends diametrically across the cap and is fixed thereto. In one embodiment, the pin extends through a pair of diametrically disposed apertures at the depending lip of the cap which are located so as to cause the pin to engage the ratcheting recesses of the body member to permit unidirectionally motion of the cap, and so control the tension on the floss. In a second embodiment, to achieve unidirectional rotation of the cap, the cap has a series of complementary ratcheting recesses formed around the inner surface of the depending lip so as to engage the body member ratcheting recesses. In the second embodiment, the pin resiliently holds the cap ratcheting recesses against the body member ratcheting recesses, either by being disposed within the cap and extending through a pair of diametrically disposed apertures formed in the depending lip above the ratcheting recesses, or by being disposed in an inwardly curved diametrical groove formed on the exterior surface of the cap so as to extend through an axial aperture formed in the cap and through which the axle extends.

BRIEF DESCRIPTION OF THE DRAWING

The invention may be more readily understood by referring to the accompanying drawing, in which:

FIG. 1 is a perspective view of a dental floss holder according to a first embodiment the present invention;

FIG. 2 is an exploded perspective view thereof;

FIG. 3 is a side elevational view, partly in section, thereof;

FIG. 4 is a fragmentary sectional view of a portion of the holder ratcheting mechanism thereof;

FIG. 5 is a perspective view of a dental floss holder according to a second embodiment of the present invention;

FIG. 6 is an exploded perspective view thereof;

FIG. 7 is a side elevational view, partly in section, thereof;

FIG. 8 is a fragmentary sectional view of a portion of the holder ratcheting mechanism thereof;

DETAILED DESCRIPTION OF THE PREFERRED EMBODIMENTS

Figure 9:
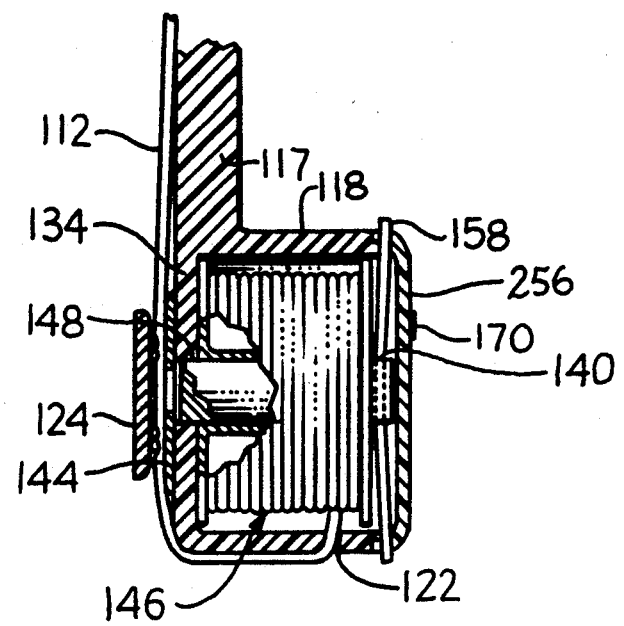
FIG. 9 is a side elevational view, partly in section, of a third embodiment of the present invention.

Referring now to FIG. 1, there is shown a perspective view of a first embodiment of a dental floss holder according to the present invention, illustrating the manner in which dental floss is spanned between a first prong 14 and a second prong of the holder. The holder 10 has a body portion 18 which is generally cylindrical and to which the prongs 14 and 16 are connected by a stem 17 so as to be in a "wishbone" disposition and generally normal to the main body 18. A space 20 is formed between the prongs 14, 16 to provide an access way to the spanned floss 12 in order to assist in the flossing operation. A slot 22 (not shown, see FIG. 2) is formed in the body portion 18 opposite the stem 17 to provide a passageway through which the floss 12 emerges from within the body portion 18. As is seen in FIG. 1, the floss 12 passes from the main body portion 18 over a slotted head portion 24 of an axle 38 (see FIG. 2) through a slot 26 formed therein. Then, the floss passes around a floss separator boss 28 formed on the stem 17 and is guided onto the prong 14 and around a prong tip slot 30 (see FIG. 2) by a deep slot 30A. The floss 12 then passes to a similar tip slot 32 formed on the second prong 16. From the tip slot 32, the floss passes through a deep slot 32A formed in the second prong 16 to the floss separator boss 28 on the stem 17 and then to and under the slotted head 24, and around the axle 38, about which the floss 12 is tightly wound, preferably twice, in order to lock the floss between the slotted head 24 and a slotted washer 44 (see FIG. 3) which is held against the main body portion 18 at a generally closed face 34 formed thereon.

Referring now to FIG. 2, the axle 38 which terminates in the slotted head 24 at one end has, at the other end, a transverse passageway 40 formed therein. A slotted washer 44 is mounted on the axle 38 adjacent the slotted head 24 by a pair of teeth 44A which engage the slot 26 so as to permit limited axial movement relative between the washer 44 and the slotted head 24. The floss passes around the axle 38 and is clamped between the slotted head 24 and the washer 44. The body portion 18 has a central axial bore 46 formed therein which terminates in a small aperture 48 (see FIG. 3), formed in the generally enclosed face 34 so as to be axially aligned with the central bore 46. At its opposite end, the axial bore 46 opens on to a series of ratcheting recesses 50 formed about the periphery of the body portion 18 opposite the generally closed face 34.

A spool 54 holding the floss 12 is adapted to fit within the axial bore 46. The spool 54 is inserted within the bore 46 so that the axle 38 extends through a central bore 52 in the spool. A locking cap 56 encloses the spool 54 within the bore 46. A locking pin 58 is disposed in a diametrical recess 60 formed in the outer face of the locking cap 56 so as to extend across a bore 62 formed in the locking cap 56. The axle 38 extends through the bore 62 (see FIG. 3). The diametrical recess 60 varies in depth along its length, having the greatest depth at the bore 62 and lessening in depth as the recess 60 extends toward the periphery of the locking cap 56. Thus, the locking pin, when disposed in the diametrical recess 60 so as to extend through the transverse passageway 40 on the axle 38 is deflected inwardly toward the axial bore 46, thereby holding the locking cap 56 snugly against the main body portion 18.

As is seen in FIG. 4, the ratcheting recesses 50 on the main body portion 18 are unidirectional in nature, that is, each recess 50 has a stop face 58 and a deflection face 50B. The locking cap 56 has a depending lip 64 around the periphery thereof. Immediately within the depending lip 64 is a circular shoulder of ratcheting recesses 66 which are complementary to the ratcheting recesses 50 of the main body portion. In other words, when the shoulder ratcheting recesses 66 engage the ratcheting recesses 50, only unidirectional relative movement between the main body portion 18 and the locking cap 56 is possible. The main body portion 18 has an external shoulder 68 formed adjacent the ratcheting recesses 50 so that the locking cap 56 may be snugly mounted on the main body portion 18 by means of the depending lip 64 enclosing the shoulder 68.

Referring back to FIG. 3, the floss holder 10 is shown partially in section, illustrating the means by which the floss 12 is passed from the axial bore 46 around the axle 38 between the slotted head 34 and the washer 44, and from underneath the slotted head 34 to the prongs 14, 16 and back to the slotted head 34, as is shown in FIG. 1. The floss end representing any excess floss after wrapping around the axle 38, is then brought to the face of the locking cap 56 and cut off by means of a cutter blade assembly 70. When it is desired to increase the tension on the floss 12 spanned between the prongs 14 and 16, the locking cap 58 is rotated manually so as to increase the tension on the floss 12 in the slot 26.

The dental floss holder 10 of FIGS. 1 through 4 employs a simple locking arrangement to enable the user to readily lock the spanned floss, thereby permitting a tensioned length of floss to be formed quickly and with a minimum of effort for immediate use. In use, the holder 10 is partially inserted into the mouth of the user so that the prongs 14, 16 are disposed, one to the lingual and one to the labial side of the tooth structure to be cleaned. The floss 12 is then worked between adjacent teeth in order to provide the cleaning function. While the teeth are being so cleaned, increased tension may be supplied by rotation of the locking cap as previously described. When the floss has become worn, it is unwound from the slotted head 24 and new floss pulled from the spool 54 and spanned between the prongs 14, 16 and locked by means of the slotted head 24 as previously described. New floss is then available for use in cleaning additional teeth.

Referring now to FIG. 5, there is shown a perspective view of a second embodiment of a dental floss holder according to the present invention illustrating the manner in which dental floss is spanned between a first prong 114 and a second prong of the holder. The holder 110 has a body portion 118 which is generally cylindrical and to which the prongs 114 and 116 are connected by a stem 117 so as to be in a "wishbone" disposition and generally normal to the main body 118. A space 120 is formed between the prongs 114, 116 to provide an access way to the spanned floss 112 in order to assist in the flossing operation. A slot 122 (not shown, see FIG. 6) is formed in the body portion 118 opposite the stem 117 to provide a passageway through which the floss 112 emerges from within the body portion 118. As is seen in FIG. 5, the floss 112 passes from the main body portion 118 over a slotted head portion 124 of an axle 138 (see FIG. 6) through a slot 126 formed therein. Then, the floss passes around a floss separator boss 128 formed on the stem 117 and is guided onto the prong 114 and around a prong tip slot 130 (see FIG. 6) by a deep slot 130A. The floss 112 then passes to a similar tip slot 132 formed on the second prong 116. From the tip slot 132, the floss passes through a deep slot 132A formed in the second prong 116 to the floss separator boss 128 on the stem 117 and then to and under the slotted head 124, and around the axle 138, about which the floss 112 is tightly wound, preferably twice, in order to lock the floss between the slotted head 124 and a slotted washer 144 (see FIG. 7) which is held against the main body portion 118 at a generally closed face 134 formed thereon.

Referring now to FIG. 6, the axle 138 which terminates in the slotted head 124 at one end has, at the other end, a transverse passageway 140 formed therein A slotted washer 144 is mounted on the axle 138 adjacent the slotted head 124 by a pair or teeth 144A which engage the slot 126 so as to permit limited axial movement relative between the washer 144 and the slotted head 124 The floss passes around the axle 138 and is clamped between the slotted head 124 and the washer 144. The body portion 118 has a central axial bore 146 formed therein which terminates in a small aperture 148 (see FIG. 7), formed in the generally enclosed face 134 so as to be axially aligned with the central bore 146. At its opposite end, the axial bore 146 opens on to a series of ratcheting recesses 150 formed about the periphery of the body portion 118 opposite the generally closed face 134.

A spool 154 holding the floss 112 is adapted to fit within the axial bore 146. The spool 154 is inserted within the bore 146 so that the axle 138 extends through a central bore 152 in the spool. A locking cap 156, having a cross-sectional configuration complementary to that of the main body portion axial bore 146, encloses the spool 154 within the bore 146. A straight locking pin 158 extends diametrically across the interior of the locking cap 156 and through a pair of diametrically oppositely disposed locking apertures 160 formed in the locking cap 156. The axle 138 has a tip 138A which abuts the interior surface of the locking cap 156 (see FIG. 7). The locking pin 158, when passing through the locking apertures 160 so as to extend diametrically across the locking cap 158 as shown in FIG. 7, is deflected inwardly toward the axial bore 146 by passing through the transverse aperture 140 formed in the pin 138, thereby holding the locking cap 156 snugly against the main body portion 118.

As is seen in FIG. 8, the ratcheting recesses 150 on the main body portion 118 are unidirectional in nature, that is, each recess 150 has a stop face 158 and a deflection face 150B. The locking cap 156 has a depending lip 164 around the periphery thereof. Immediately within the depending lip 164 is a circular shoulder of ratcheting recesses 166 which are complementary to the ratcheting recesses 150 of the main body portion. In other words, when the shoulder ratcheting recesses 166 engage the ratcheting recesses 150, only unidirectional relative movement between the main body portion 118 and the locking cap 156 is possible. The main body portion 118 has a external shoulder 168 formed adjacent the ratcheting recesses 150 so that the locking cap 156 may be snugly mounted on the main body portion 118 by means of the depending lip 164 enclosing the shoulder 168.

Referring back to FIG. 7, the floss holder 110 is shown partially in section, illustrating the means by which the floss 112 is passed from the axial bore 146 around the axle 138 between the slotted head 134 and the washer 144, and from underneath the slotted head 134 to the prongs 114, 116 and back to the slotted head 134, as is shown in FIG. 5. The floss end representing any excess floss after wrapping around the axle 138, is then brought to the face of the locking cap 156 and cut off by means of a cutter blade assembly 170. When it is desired to increase the tension on the floss 112 spanned between the prongs 114 and 116, the locking cap 158 is rotated manually so as to increase the tension on the floss 112 in the slot 126.

The dental floss holder 110 of the second embodiment of the present invention employs a simple locking arrangement to enable the user to readily lock the spanned floss, thereby permitting a tensioned length of floss to be formed quickly and with a minimum of effort for immediate use in the same manner as was heretofore described with respect to the first embodiment shown in FIGS. 1 through 4.

Figure 10:
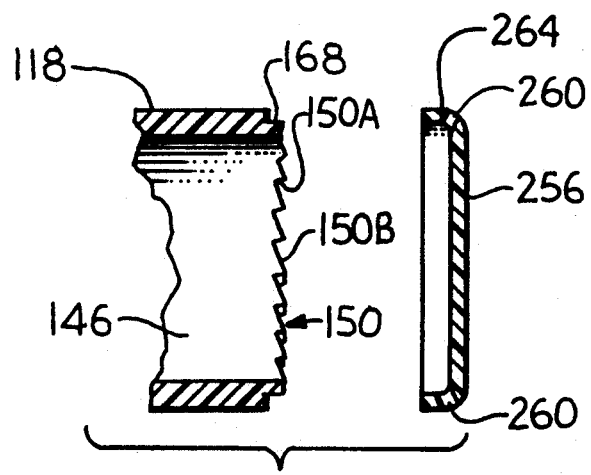
FIG. 10 is a fragmentary sectional view of a portion of the holder ratcheting mechanism thereof.

Referring now to FIG. 9, there is shown another alternate embodiment of the present invention utilizing components generally similar to those shown in the embodiment of FIGS. 5-8. However, the embodiment of FIGS. 9 and 10 utilizes a cap 256 whose depending lip 264 is foreshortened from the length of the depending lip 164 in the cap 156. In addition, the ratcheting teeth 166 and the cap 156 are eliminated in the cap 256. The pin 158 extends through a pair of diametrically disposed apertures 260 formed in the cap 256 at its ends, and, in its central portion, the pin extends through the aperture 140 in the axle 138. Because of the foreshortening of the lip 264 in the cap 256, the ends of the pin 158 may directionally engage the ratcheting recesses 150 in the body member 118 so as to provide for unidirectional rotation of the cap 256 and so the spool 154 to control the tension on the floss 112, as has been described heretofore. The remaining components of the embodiment of FIGS. 9 and 10 are identical to those in the embodiment of FIGS. 5-8, and, consequently, like reference numerals in the Figures refer to like components.

I claim:

1. In a dental floss holder of the type having a body member with an axial bore formed therein so as to extend from one side thereof, which is open and on which unidirectional ratcheting teeth are circularly disposed in axial alignment with the bore, to the other body side which is closed but with a small diameter opening extending there through, a pair of prongs extending outwardly laterally from the body member normal to the bore in a wishbone configuration, each of said prongs having a deep floss receiving groove formed longitudinally along its outer surface, and each prong terminating in a tip across which the groove extends toward the other prong, an axle extending through the body member, a spool holding dental floss mounted on the axle within the body member, and a passageway formed on the body member for passing the floss from the spool through the body member, the combination of:

a locking cap of circular cross-sectional configuration complementary to the cross-sectional configuration of the body member, said cap having a peripheral lip depending therefrom so as to enclose the main body ratcheting recesses when the cap is disposed on the main body member, and a circular shoulder formed within the recess formed by the lip and adjacent thereto, said shoulder having ratcheting teeth formed thereon so as to be complementary to the main body ratcheting teeth and engageable therewith when the cap is mounted on the main body member; and locking cap attaching means connected between said locking cap and said body member for attaching said cap to said axle so as to hold said cap ratcheting teeth in engagement with said main body ratcheting teeth, said locking cap attaching means including a straight pin extending diametrically across said locking cap and through a transverse passageway formed in said axle and pin engaging means formed on said locking cap and operable when engaged by said pin while extending through said axle transverse passageway to hold said pin in a deflected disposition so as to urge the cap ratcheting teeth against the main body ratcheting teeth.

2. A dental floss holder according to claim 1 including floss cutting means mounted on said locking cap on the side thereof opposite said cap ratcheting teeth.

3. A dental floss holder according to claim 1, and in which the pin engaging means is comprised by a pair of apertures formed in said locking cap adjacent said depending lip so as to be diametrically opposite one another for holding opposite ends or said straight pin extending through said axle transverse passageway in said deflected disposition.

4. A dental floss holder according to claim 3 including floss cutting means mounted on said locking cap on the side thereof opposite said cap ratcheting teeth.

5. In a dental floss holder of the type having a body member with an axial bore formed therein so as to extend from one side thereof, which is open and on which unidirectional ratcheting teeth are circularly disposed in axial alignment with the bore, to the other body side which is closed but with a small diameter opening extending there through, a pair of prongs extending outwardly laterally from the body member normal to the bore in a wishbone configuration, each of said prongs having a deep floss receiving groove formed longitudinally along its outer surface, and each prong terminating in a tip across which the groove extends toward the other prong, an axle extending through the body member, a spool holding dental floss mounted on the axle within the body member, and a passageway formed on the body member for passing the floss from the spool through the body member, the combination of:

a locking cap of circular cross-sectional configuration complementary to the cross-sectional configuration of the body member, said cap having a peripheral lip depending therefrom so as to enclose the main body ratcheting recesses when the cap is disposed on the main body member; and locking cap attaching means connected between said locking cap and said body member for attaching said cap to said axle so as to hold said cap in engagement with said main body ratcheting teeth, said locking cap attaching means including a straight pin extending diametrically across said locking cap and through a transverse passageway formed in said axle, and a pair of apertures formed in said locking cap so as to be diametrically opposite one another for holding opposite ends of said straight pin extending through said axle transverse passageway against said main body ratcheting recesses.

6. A dental floss holder according to claim 5 including floss cutting means mounted on said locking cap on the side thereof opposite said cap peripheral lip.

* * * * *